United States Patent [19]

Botzolakis et al.

[11] Patent Number: 4,807,465
[45] Date of Patent: Feb. 28, 1989

[54] APPARATUS FOR MEASURING CAPSULE PLUG, GRANULE AND PELLET HARDNESS

[75] Inventors: John E. Botzolakis, Randolph; Michael R. Harris, Hackettstown; Russell U. Nesbitt, Somerville, all of N.J.

[73] Assignee: Warner-Lambert Company, Morris Plains, N.J.

[21] Appl. No.: 158,012

[22] Filed: Feb. 19, 1988

[51] Int. Cl.⁴ .................. B23Q 17/20; G01N 3/08; G01N 3/20

[52] U.S. Cl. .......................................... 73/78; 73/521; 73/852; 73/860

[58] Field of Search ................ 73/78, 81-83, 73/85, 821, 849, 851-853, 856, 860

[56] References Cited

U.S. PATENT DOCUMENTS

| | | | |
|---|---|---|---|
| 1,200,086 | 10/1916 | Cruser | 73/852 |
| 1,827,805 | 10/1931 | Watts | 73/851 |
| 3,142,174 | 7/1964 | Baker | 73/852 |
| 3,323,356 | 6/1967 | Arias | 73/852 |
| 4,059,990 | 11/1977 | Glover et al. | 73/81 |
| 4,094,188 | 6/1978 | Bellovia et al. | 73/81 |
| 4,542,646 | 9/1985 | Smith et al. | 73/821 |
| 4,635,471 | 1/1987 | Rogers et al. | 73/81 |

FOREIGN PATENT DOCUMENTS 993829 6/1965 United Kingdom ............. 73/851

Primary Examiner—Stewart J. Levy
Assistant Examiner—Robert R. Raevis
Attorney, Agent, or Firm—Howard Olevsky; Daniel A. Scola, Jr.

[57] ABSTRACT

Apparatus for measuring the hardness of capsule plugs, granules and pellets, in which a power stand (11) has a base (12) and gear motor (15) for driving a replaceable probe (25) toward a test subject supported on the base. A test subject holder (27) is placed on the base for holding the test subject, and comprises spaced apart first and second support plates (28, 30) fixed relative to one another with a third support plate (29) movable therebetween to define a space variable between zero and a predetermined maximum. Accordingly, a test subject may be held on the support for testing in a selected one of a variety of modes, including crushing, bending and cutting, depending on the spacing of the plates and the probe selected.

11 Claims, 3 Drawing Sheets

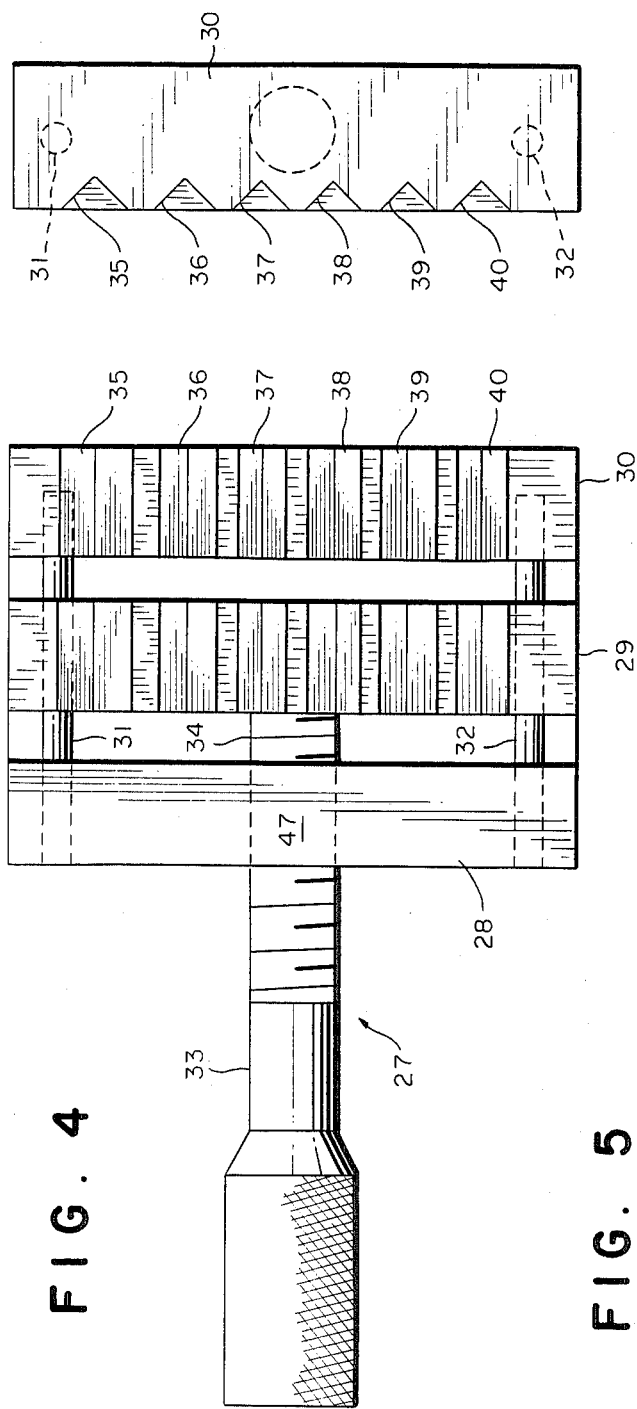
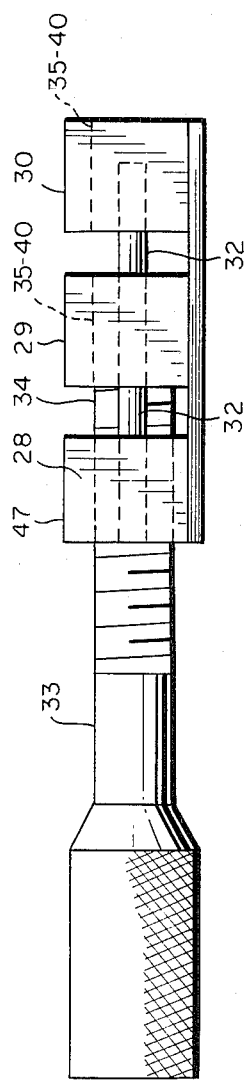
FIG. 4  FIG. 5  FIG. 6

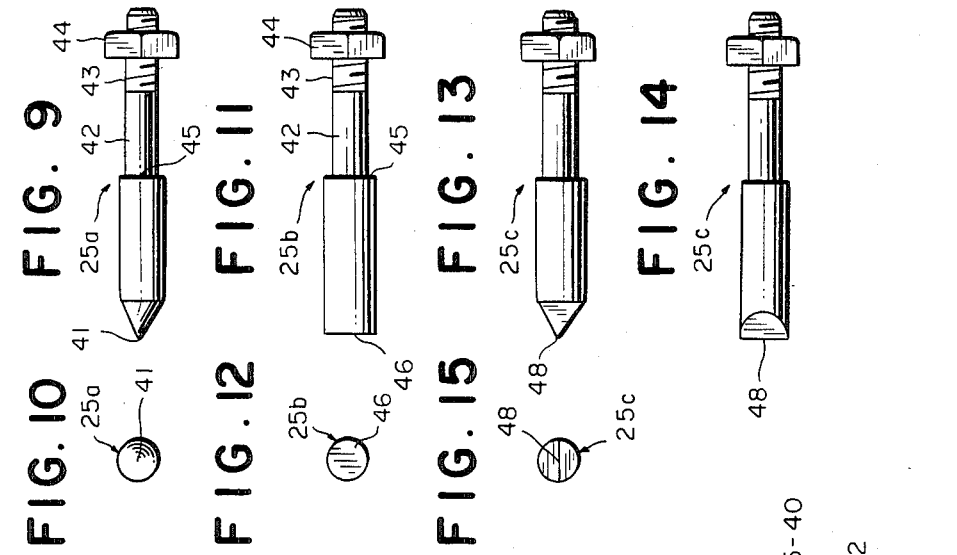
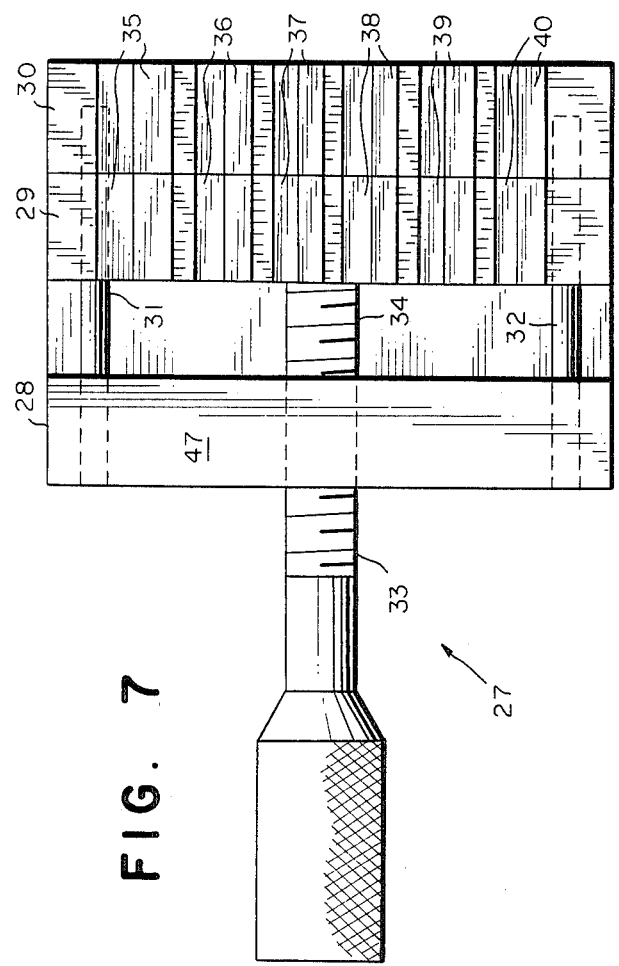
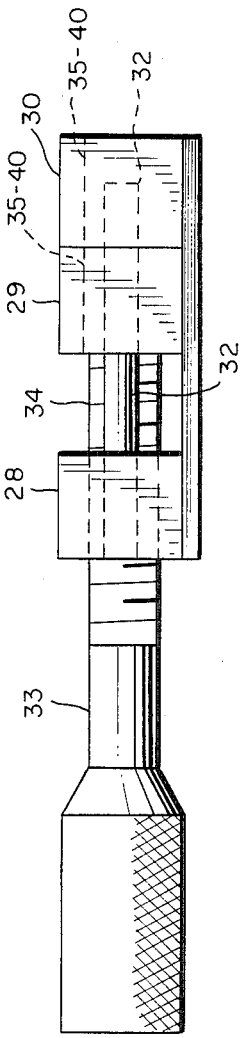

APPARATUS FOR MEASURING CAPSULE PLUG, GRANULE AND PELLET HARDNESS

FIELD OF THE INVENTION

This invention relates to measuring and testing apparatus, and more particularly, to an apparatus for accurately measuring the hardness of capsule plugs, granules and pellets.

PRIOR ART

In the manufacture of pharmaceuticals, and particularly hard gelatin capsules, high speed machinery is used to produce and fill the capsules. In order to facilitate this process, the pharmaceutical mixtures used to fill the capsules are compacted into a plug which, in many cases, remains intact when inserted into the capsule body. The cohesiveness of the plug depends upon the compressive force employed during encapsulation and the type of excipients used in the formulation. The degree of plug hardness is important since it may affect the in-vitro disintegration of the capsule and dissolution of the active component. Similarly, the hardness of granules and/or pellets depends upon the type of excipients and binder used as well as the equipment employed in their formation. Granule strength, for example, will affect particle size distribution of the granules and hence their compressibility into tablets. Pellets, on the other hand, have to be able to withstand the various forces encountered during the various stages of processing and handling. Thus, it is important that the hardness of these materials be controlled during the manufacturing process. Unfortunately, there is not presently any commercially available means for accurately measuring the hardness of these materials whereby manufacturing adjustments can be made to achieve a desired result.

Numerous devices do exist, however, for testing or measuring the hardness of tablets. For example, U.S. Pat. Nos. 4,409,843 and 4,542,646 disclose two such devices. Other patents which disclose apparatus for measuring the hardness or deformability of materials are 2,670,624, 2,671,344 and 3,323,356. These prior art devices are not satisfactory for measuring the hardness of capsule plugs, granules and pellets, however, since the forces involved in testing such materials are in the lower end of the scale of tablet hardness (usually less than about 1 kg.). In addition, capsule plug, granule and pellet test subjects are small or cylindrical and the forces measured are fundamentally different from those of tablets. Although some of these devices (see U.S. Pat. Nos. 4,049,843 and 4,542,646, for example) are suitable for testing or measuring tablet hardness, they do not have the requisite sensitivity for accurately measuring the hardness of granules, pellets and capsule plugs. In addition, they are specifically constructed for measuring the hardness of tablets and would not be suitable for use in measuring the hardness of granules, pellets and capsule plugs.

SUMMARY OF THE INVENTION

In accordance with the present invention, an apparatus is provided for accurately measuring the hardness of capsule plugs, granules and pellets. In the invention, a novel support is provided for holding capsule plug specimens during the testing procedure, and a very sensitive load cell is mounted on a movable slide driven by a motor and gear arrangement, with a suitable ram or probe affixed to the load cell for movement toward an anvil or specimen support on which a capsule plug, granule or pellet is placed in position to be contacted by the probe. An adjustable speed control is connected with the motor to regulate the speed of movement of the slide and probe, and an amplifier and recorder are connected with the load cell/transducer to amplify and record the results of the measurement being taken.

The unique specimen holder or support includes movable sections or plates mounted for movement toward and away from one another to selectively provide spaced apart supports for a capsule plug, for example, so that a bending force can be applied to the specimen, or to provide support throughout the length of the specimen so that the specimen can be cut. The specimen holder also has a plurality of differently sized recesses in its top surface for holding differently sized specimens.

The ram or probe is removably mounted in the load cell and any one of a variety of differently configured probes may be easily mounted to the load cell for performing different tests on different specimens.

BRIEF DESCRIPTION OF THE DRAWINGS

The foregoing and other objects and advantages of the invention will become apparent from the following detailed description and claims taken in conjunction with the appended drawings, wherein like reference characters designate like parts throughout the several views and wherein:

FIG. 4 is an enlarged top plan view of the specimen holder of the invention;

FIG. 5 is a side view in elevation of the holder of FIG. 4;

FIG. 6 is an end view of the holder of FIG. 4;

FIG. 7 is a view similar to FIG. 4, but showing the holder in a differently adjusted position;

FIG. 8 is a view in side elevation of the adjusted holder of FIG. 7;

FIG. 9 is a side view of one of the probes which can be used with the invention;

FIG. 10 is an end view of the probe of FIG. 9;

FIG. 11 is a side view of another form of probe;

FIG. 12 is an end view of the probe of FIG. 11;

FIGS. 13 and 14 are side and top views, respectively of yet another probe; and

FIG. 15 is an end view of the probe of FIGS. 13 and 14.

DESCRIPTION OF THE PREFERRED EMBODIMENTS

Figure 1:
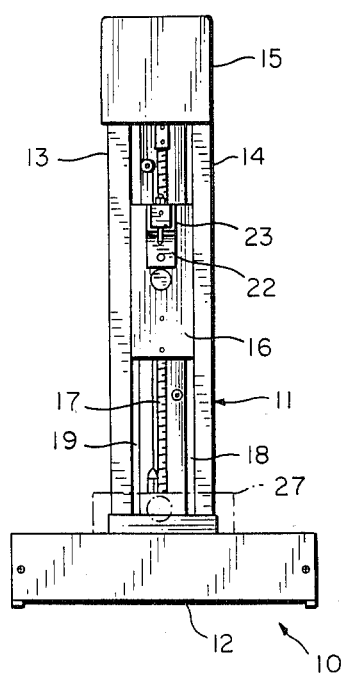
FIG. 1 is a front view in elevation of an apparatus in accordance with the invention.
Figure 2:
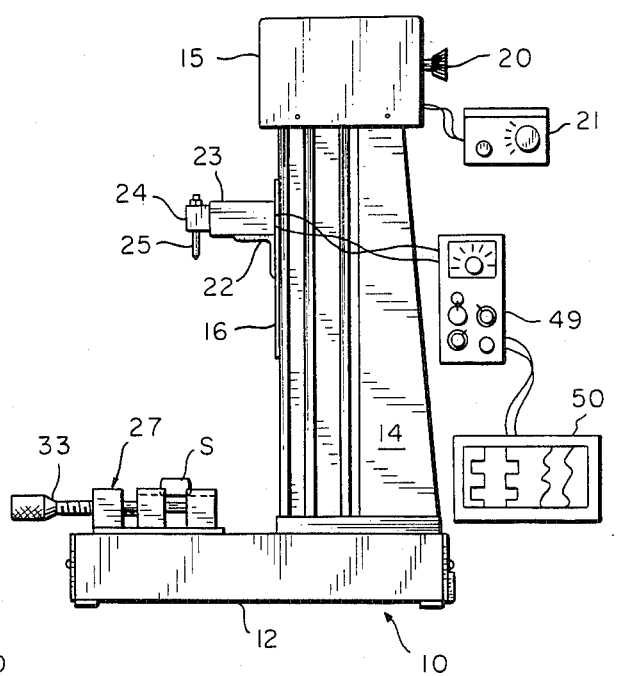
FIG. 2 is a side view in elevation of the apparatus of FIG. 1.
Figure 3:
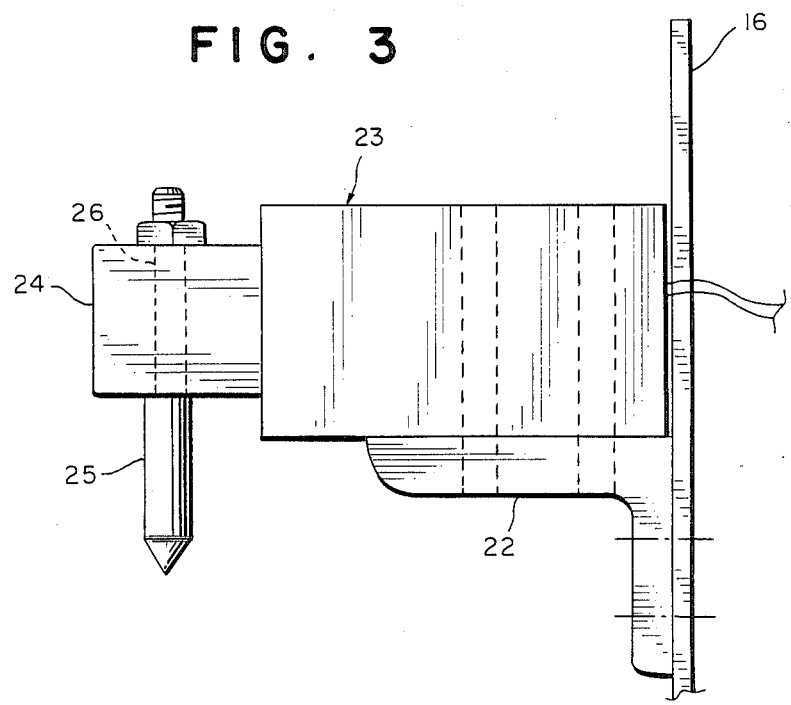
FIG. 3 is an enlarged side view of the load cell and its mount.

The apparatus for measuring capsule plug, granule and pellet hardness is indicated generally at 10 in FIGS. 1 and 2 and comprises a motorized power stand 11 having a rectangular base 12, vertically extending upright frame members 13 and 14 and a gear motor (not shown) and cover 15. A vertically movable slide 16 is carried on a threaded rod 17 extending between the motor and base, for movement toward and away from the base on guide rails 18 and 19. A manual control knob 20 is connected with the drive gearing (not shown) inside the cover 15 for manual control of movement of the slide 16, and an adjustable speed control 21 is connected with the motor for accurate control of the speed of the motor, movement of the slide, and rate of force application. The power stand can comprise, for example, a Unislide RVB 4000 series model having a Bodine Series N-1R gear motor and cover, and the speed control can comprise a Minarik adjustable speed control, model SL-15.

An angle bracket 22 is affixed to the front of the slide 16 and a mini load cell/strain gauge transducer 23 is mounted on the angle bracket. The load cell has a movable arm 24 which projects horizontally beyond the angle bracket, and a vertically extending probe or ram 25 is removably mounted in an opening 26 in the arm. The strain gauge transducer may comprise a Pacific Sensors mini load cell, having a range of 0–2000 grams.

A specimen support 27 is placed on the base in vertical alignment with the probe 25, and comprises a plurality of generally rectangularly shaped bar-like plates or sections 28, 29 and 30, with plates 28 and 30 being fixed relative to one another in spaced apart relationship and having guide pins 31 and 32 extending therebetween adjacent their opposite ends. The center plate 29 is movable on the pins toward and away from plate 30. An adjustment pin 33 is threaded through plate 28 and is connected at its inner end 34 with plate 29, whereby rotation of pin 33 causes plate 29 to move toward or away from plate 30, depending upon the direction of rotation of the pin 33. In this way, the space between plates 29 and 30 can be adjusted from a maximum with plates 28 and 29 abutting one another, to a minimum or substantially zero clearance with plates 29 and 30 abutting one another.

Plates 29 and 30 have a series of aligned, transversely extending V-shaped recesses 35 through 40 formed in the upper surfaces thereof, defining support channels for holding differently sized specimens S while they are being engaged by the probe. For instance, the channels vary in width from 13/32 inch at channel 35 to 3/8 inch at channel 36, 11/32 inch at channel 37, 3/8 inch at channels 38 and 39, and 5/16 inch at channel 40. Obviously, other sizes could be utilized, but the dimensions given accommodate typical capsule plug sizes. Thus, various size capsule plugs can be supported in the respective channels.

Probe 25 can have a variety of shapes, as shown at 25a, 25b and 25c in FIGS. 9 through 14. In FIGS. 9 and 10, the probe 25a has a conically shaped point 41 and would be used, for example, in an indentation test performed on capsules. The reduced diameter shank portion 42 is extended through the opening 26 in the arm 24 of the load cell 23, with the threaded end 43 projecting beyond the arm and suitable fastening means, such as nut 44 engaged thereon. Tightening of nut 44 on the threaded end 43 draws shoulder 45 against the bottom side of arm 24 to securely and rigidly fasten the probe to the arm of the load cell.

Probe 25b, on the other hand, has a flat end 46 and would be used for testing pellets or granules. In this test, the pellet or granule would be placed on the flat top surface 47 of plate 28 of support 27, or directly on the base 12. The probe 25b would then be slowly lowered against the pellet or granule until the pellet or granule experienced stress failure.

Probe 25c has a chisel or blade-like point 48 and is used for performing bending or cutting tests on capsules. For instance, the strength of a capsule may vary along its length and by applying a bending force to the capsule, the weakest point or level of strength would be discovered. The bending moment may be varied by simply adjusting the spacing between plates 29 and 30 of specimen support 27.

All of the above tests are performed to failure of the specimen, and the force required to effect a stress failure of the specimen is measured and converted into an electrical signal by the load cell/transducer 23. This signal is amplified by an amplifier 49 and used to operate a chart recorder 50, which records the force. With this information, adjustments can be made to the manufacturing process, as necessary, in order to achieve a satisfactory hardness of the capsule plugs, granules or pellets being manufactured.

Operation of the system is relatively simple and fast. Initial set up of the system involves balancing the amplifier and positioning the load cell and probe above the test subject. The motor is then energized to move the load cell and probe downwardly against the test subject. When capsule plugs are to be tested, the probe 25c is used to break (by bending) or cut the capsule plugs. The plugs are placed in a suitable channel in the support 27 and the blade-like edge 48 is aligned transversely to the longitudinal axis of the plug. The space between plates 29 and 30 may set to a desired width or closed, depending upon whether a bending or cutting mode is desired in the test.

For testing pellets or granules, the probe 25b is used. In this test, the pellets or granules are simply placed on the flat upper surface of the support plate section 28, or on the top of the base 12, and the probe is moved against the test subject until stress failure of the test subject occurs.

The hardness values of nonpareil seeds of various sizes are shown in Table 1; the hardness values of anhydrous lactose capsule plugs compressed to various degrees and measured by two methods are shown in Table 2; and the hardness values along the length of plugs for two filler systems are shown in Table 3.

TABLE 1

| Hardness of Various Sizes of Pellets | |
|---|---|
| Pellet size | Hardness (g) |
| 16–18 mesh | 906 |
| 18–20 mesh | 667 |
| 20–25 mesh | 443 |

TABLE 2

| Hardness of Anhydrous Lactose Capsule Plugs Tamped to Various Degrees and Measured by Two Methods | |
|---|---|
| Tamping/Method | Hardness (g) |
| 1 tamp/bending | 24.6 |
| 1 tamp/cutting | 29.9 |
| 5 tamps/bending | 52.3 |
| 5 tamps/cutting | 56.2 |

TABLE 3

| Hardness Measurements Along the Length of Plugs for Two Filler Systems (cutting Mode) | | |
|---|---|---|
| Filler/Part of Plug | | Hardness (g) |
| Lactose | top | 69.2 |
| | middle | 56.2 |
| | bottom | 38.9 |
| Avicel | top | 282.0 |
| | middle | 248.5 |
| | bottom | 167.5 |

Although the invention has been described with reference to particular embodiments, it is to be understood that these embodiments are merely illustrative of the application of the principles of the invention. Numerous modifications may be made therein and other arrangements may be devised without departing from the spirit and scope of the invention.

We claim:

1. Apparatus for measuring capsule plug, pellet and granule hardness, comprising:
   a powered stand having a base or anvil and a movable member mounted for movement toward and away from the base;
   a load cell carried by the movable member for movement with the member toward and away from the base;
   a probe carried by the load cell in a position for contacting a test subject on the base; and
   test subject support means on the base for holding a test subject, said support means including plural support sections movable relative to one another to define a variable space therebetween, whereby the support sections may be moved apart for placement of a test subject on the plural support sections in spanning relationship to the space for contact by the probe in the area of the test subject located between the support sections for exerting a bending moment on the test subject, and the support sections may be moved into contiguous relationship with one another to define an uninterrupted support surface on which a test subject may be placed for contact by the probe to exert a crushing or cutting force on the test subject.

2. Apparatus as claimed in claim 1, wherein:
   the test subject support sections have an upper surface, and differently sized recesses are formed in the upper surface for holding differently sized test subjects.

3. Apparatus as claimed in claim 2, wherein:
   the support sections are configured for holding capsule plugs, and the recesses comprise channels having a V-shaped transverse cross-section, the channels in one support section being aligned with the channels in another section so that when one end of a section, the other end of the plug may be supported in a complementally shaped and aligned channel in the other support section.

4. Apparatus as claimed in claim 3, wherein:
   the width of the V-shaped channels varies from one channel to the other, whereby a plurality of differently sized capsule plugs may be properly supported on the test subject support means by placement of the capsule plug in an appropriately sized channel.

5. Apparatus as claimed in any one of claims 1 through 4, wherein:
   the load cell has a range of from about 0 up to about 2000 grams and produces a signal representative of the force exerted by the probe against the test subject;
   an amplifier is connected with the load cell to amplify the signal produced thereby; and
   a chart recorder is connected with the amplifier to receive the amplified signal and produce a chart recording of the force exerted on the test subject.

6. Apparatus as claimed in claim 5, wherein:
   the test subject support means comprises first and second spaced apart support plates fixed relative to one another;
   guide pin means extending between the first and second support sections;
   a third, movable support section carried on said guide pin means in the space between the first and second support sections for movement toward and away from said second support section to define a variable space therebetween; and
   adjustment means connected between said first support section and said third support section for effecting movement of said third support section toward and away from the second support section to increase or decrease the variable space between the second and third support sections.

7. Apparatus as claimed in claim 1, wherein:
   the probe is removably mounted in the load cell for substitution of different probes.

8. Apparatus as claimed in claim 1 or claim 7, wherein:
   the probe has a flat end for contact with the test subject for exerting a crushing force on the test subject, for use in the measurement of the hardness of granules and pellets.

9. Apparatus as claimed in claim 1 or claim 7, wherein:
   the probe has a blade-like end for contact with the test subject to exert a cutting or bending force on the test subject, depending upon whether the test subject is supported throughout its length or only at the ends, respectively.

10. In an apparatus for measuring the hardness of capsule plugs, granules and pellets, wherein a movable probe is mounted for movement toward and away from a base on which a test subject may be supported for contact by the probe to cause stress failure of the test subject, and including means for measuring the force applied by the probe to the test subject, the improvement comprising:
    a test subject support means for holding the test subject while it is being contacted by the probe, said support means having a plurality of support sections movable into juxtaposed relationship with one another to define a continuous support surface for supporting a specimen continuously throughout its length, and movable away from one another into mutually spaced apart relationship, whereby spaced sections are provided for supporting a test subject at spaced locations.

11. Apparatus as claimed in any one of claims 1 through 4, 7 or 10, wherein:
    the test subject support means comprises first and second spaced apart support sections fixed relative to one another;
    guide pin means extending between the first and second support sections;
    a third, movable support section carried on said guide pin means in the space between the first and second support sections for movement toward and away from said second support section; and
    adjustment means connected between said first support section and said third support section for effecting movement of said third support section toward and away from the second support section to increase or decrease space between the second and third support sections.

* * * * *